United States Patent [19]

Gillard

[11] Patent Number: 5,187,180
[45] Date of Patent: Feb. 16, 1993

[54] (QUINOLIN-2-YLMETHOXY)HETEROTETRAHYDROCARBAZOLES AS INHIBITORS OF THE BIOSYNTHESIS OF LEUKOTRIENES

[75] Inventor: John W. Gillard, Baie d'Urfe, Canada

[73] Assignee: Merck Frosst Canada, Inc., Kirkland, Canada

[21] Appl. No.: 729,019

[22] Filed: Jul. 12, 1991

Related U.S. Application Data

[63] Continuation-in-part of Ser. No. 558,724, Jul. 26, 1990, abandoned.

[51] Int. Cl.$^5$ .................. A01N 43/42; C07D 215/36
[52] U.S. Cl. ........................ 514/312; 514/313; 514/314; 514/826; 546/153; 546/155; 546/156; 546/159; 546/162; 546/167; 546/170; 546/171; 546/172; 546/174; 546/176; 546/177
[58] Field of Search ............... 546/172, 174, 153, 155, 546/156, 159, 162, 167, 170, 171, 176, 177; 514/312, 313, 314, 826, 914

[56] References Cited

U.S. PATENT DOCUMENTS

| | | | |
|---|---|---|---|
| 4,057,559 | 11/1977 | Asselin et al. | 560/122 |
| 4,578,398 | 3/1986 | Mobilio et al. | 514/411 |
| 4,775,680 | 10/1988 | Gillard et al. | 514/411 |
| 4,783,479 | 11/1988 | Mobilio | 514/410 |
| 4,808,608 | 2/1989 | Guindon et al. | 514/411 |
| 4,920,132 | 4/1990 | Huang et al. | 514/314 |
| 4,929,626 | 5/1990 | Mohrs et al. | 514/311 |
| 4,940,719 | 7/1990 | Gillard et al. | 514/381 |
| 4,962,203 | 10/1990 | Young et al. | 546/180 |
| 4,970,215 | 11/1990 | Mohrs et al. | 514/311 |

FOREIGN PATENT DOCUMENTS

| | | |
|---|---|---|
| 0238226 | 9/1987 | European Pat. Off. . |
| 0307077 | 3/1989 | European Pat. Off. . |
| WO91/06537 | 5/1991 | PCT Int'l Appl. . |
| 1382513 | 2/1975 | United Kingdom . |

OTHER PUBLICATIONS

Mobilio et al., J. Med. Chem., 31, 2211-2217 (1988).

Primary Examiner—C. Warren Ivy
Assistant Examiner—Raymond Covington
Attorney, Agent, or Firm—Gabriel Lopez; Joseph F. DiPrima

[57] ABSTRACT

(Quinolin-2-ylmethoxy)Heterotetrahydrocarbazoles as inhibitors of the biosynthesis of leukotrienes useful in the treatment of asthma and eye inflamation.

7 Claims, No Drawings

(QUINOLIN-2-YLMETHOXY)HETEROTETRAHYDROCARBAZOLES AS INHIBITORS OF THE BIOSYNTHESIS OF LEUKOTRIENES

CROSS-REFERENCE

This is a continuation-in-part of Ser. No. 558,724, Jul. 26, 1990, pending now abandoned.

BACKGROUND OF THE INVENTION

The leukotrienes and their biological activities, especially their roles in various disease states and conditions have been described. For example, see U.S. Pat. No. 4,683,325 Jul. 28, 1987), which is incorporated herein by reference.

Several classes of compounds exhibit the ability to inhibit the biosynthesis of leukotrienes in mammals, especially humans. For example, EP 349,062 (Merck) describes a series of compounds of the general formula A:

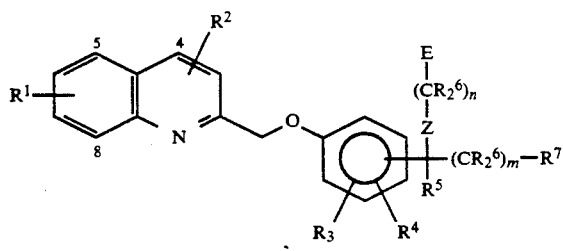

A (EP 349,062)

EP 339,416 (Bayer) and EP 344,519 (Bayer) describe compounds of Formulas B and C respectively:

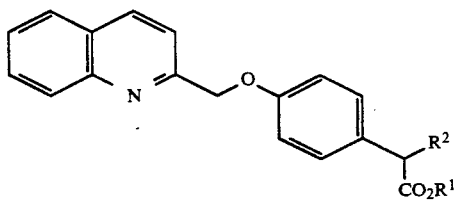

B (EP 339,416)

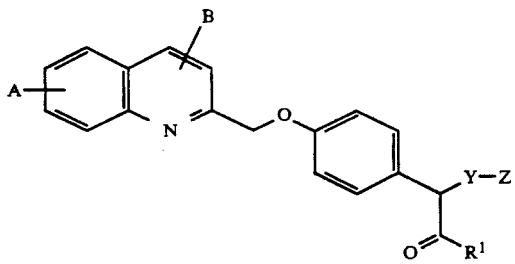

C (EP 344,519)

The above compounds differ chemically from the present invention in a major structural feature. Namely, the compounds of the present invention contain a heterotetrahydrocarbazole nucleus, which is absent from the above.

EP 353,983 (Glaxo) and JP 80/145,687 (Chem. Ab. 94, 121318) (Synthelabo) disclose azatetrahydrocarbazoles of structures D and E. Can. Pat. 1,006,875 (Ayerst) discloses oxa- and thia-tetrahydrocarbazoles of Formula F. All of these compounds differ significantly from the compounds of the present invention, in that the latter all contain a quinolinylmethoxy group, whereas none of the art compounds contain a quinoline structure.

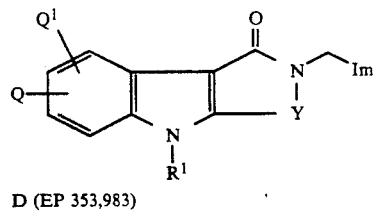

D (EP 353,983)

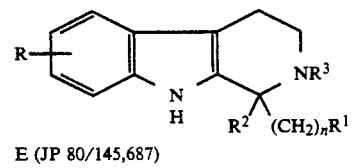

E (JP 80/145,687)

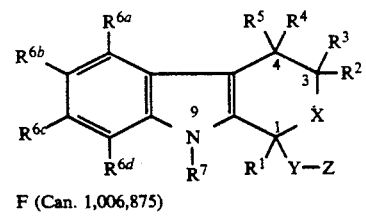

F (Can. 1,006,875)

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus, inhibition of the synthesis of such compounds will alleviate these and other leukotriene-related disease states.

DETAILED DESCRIPTION OF THE INVENTION

The present invention provides novel compounds of Formula I:

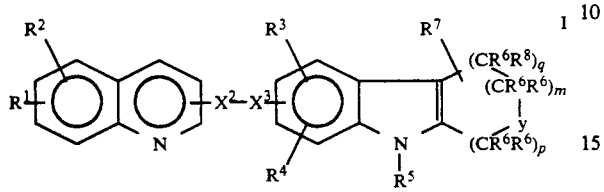

wherein:
each of $R^1$, $R^2$, $R^3$, $R^4$ and $R^{10}$ is independently hydrogen, halogen, lower alkyl, lower alkenyl, lower alkynyl, $-CF_3$, $-CN$, $-NO_2$, $-N_3$, $-C(OH)R^6R^6$, $-C(O)OR^{12}$, $-SR^{13}$, $-S(O)R^{13}$, $-S(O)_2R^{13}$, $-S(O)_2NR^{15}R^{15}$, $-C(O)NR^{15}R^{15}$, $-OR^{15}$, $-NR^{15}R^{15}$, $-C(O)R^{16}$ or $-(CH_2)_rR^{21}$;
$R^5$ is hydrogen or $X-R^9$,
$R^6$ is independently hydrogen or lower alkyl, or two $R^6$ groups on the same carbon atom are joined to form a cycloalkyl ring of 3 to 6 carbon atoms;
$R^7$ is $-(CR^6R^6)_sQ$;
$R^8$ is hydrogen, $R^9$, $-CR^{23}=CR^{24}R^{25}$, $-C(Cl)=CCl_2$ or $R^6$ plus $R^8$ on the same carbon atom may be a double bonded oxygen (=O);
$R^9$ is alkyl, alkenyl, $-(CH_2)_tPh(R^{10})_2$ or $-(CH_2)_tTh(R^{10})_2$;
$R^{11}$ is the structure of a standard amino acid except for the amino group $\alpha$ to the carboxy group, or $R^{11}$ and $R^{18}$ attached to the same nitrogen can cyclize to form a proline residue;
$R^{12}$ is hydrogen, lower alkyl or $-CH_2R^{21}$;
$R^{13}$ is $-CF_3$ or $R^{14}$;
$R^{14}$ is lower alkyl or $-(CH_2)_uR^{21}$;
$R^{15}$ is hydrogen, $-C(O)R^{16}$, $R^{14}$, or two $R^{15}$ groups on the same nitrogen may be joined to form a heterocyclic ring of 4 to 6 atoms containing up to 2 heteroatoms chosen from O, S or N;
$R^{16}$ is hydrogen, lower alkenyl, lower alkynyl, or $R^{13}$;
$R^{17}$ is $-(CH_2)_v-C(R^{18}R^{18})-(CH_2)_v-R^{19}$ or $-CH_2-C(O)NR^{15}R^{15}$;
$R^{18}$ is hydrogen or lower alkyl;
$R^{19}$ is
 a) a monocyclic or bicyclic heterocyclic radical containing from 3 to 9 nuclear carbon atoms and 1 or 2 nuclear hetero-atoms selected from N, S or O and with each ring in the heterocyclic radical being formed of 5 or 6 atoms, or
 b) the radical $W-R^{20}$;
$R^{20}$ contains up to 21 carbon atoms and is (1) a hydrocarbon radical or (2) an acyl radical of an organic acyclic or monocyclic carboxylic acid containing not more than 1 heteroatom in the ring;
$R^{21}$ is phenyl substituted with 1 or 2 $R^{22}$ groups;
$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;
$R^{23}$ is $R^{18}$ or $R^{23}$ and $R^{24}$ may form a bond;
$R^{24}$ is $R^6$ or $R^{23}$ and $R^{24}$ may form a bond;

$R^{25}$ is $R^6$;
m is 0 to 3;
p is 1 to 3
q is 0 or 1;
m+p+q is 2 to 4;
m+q is 0 to 3;
r is 0 to 2;
s is 0 to 4;
t is 0 to 3;
u is 0 to 3;
v is 0 to 3;
W is O, S, or $NR^{15}$;
X is C(O), $CR^6R^6$, $S(O)_2$, or a bond;
$X^2-X^3$ is $CH_2O$, $CH_2S$, $CH_2S(O)_2$, $CH_2CH_2$, or $CH=CH$;
Y is O, $NR^{15}$, S, S(O), or $S(O)_2$;
Q is $-C(O)NR^{11}R^{18}$, $-C(O)OR^{12}$, $-C(O)NHS(O)_2R^{13}$, $-NHS(O)_2R^{13}$, $-S(O)_2NHR^{15}$, $-C(O)NR^{15}R^{15}$, $-C(O)OR^{17}$, $-CH_2OH$, or 1H— or 2H-tetrazol-5-yl;

or the pharmaceutically acceptable salts thereof.

A preferred embodiment of Formula I is that in which:
each of $R^1$, $R^2$, $R^3$ and $R^4$ is hydrogen;
$R^5$ is $X-R^9$;
$R^8$ is $R^9$;
$R^{10}$ is hydrogen or halogen;
the $CH_2O$ is attached to the 2-position of the quinoline ring;
X is a bond;
$X^2-X^3$ is $CH_2O$;
Q is $-C(O)OR^{12}$; and the remaining substituents are as defined for Formula I; or the pharmaceutically acceptable salts thereof.

DEFINITIONS

The following abbreviations have the indicated meanings:
Ac=acetyl
$C_3H_5$=allyl
Bz=benzyl
c-=cyclo
c-$C_6H_{11}$=cyclohexyl
c-Pr=cyclopropyl
Et=ethyl
i-Pr=isopropyl
Me=methyl
Ph=phenyl
t-Bu=tert-butyl
Tz=5-tetrazolyl
Th=2- or 3-thienyl.

Alkyl, alkenyl, and alkynyl are intended to include linear, branched, and cyclic structures and combinations thereof.

The term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

The term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

The term "alkenyl" includes "lower alkenyl" and extends to cover carbon fragments having up to 20 carbon atoms. Examples of alkenyl include oct-2-en-1-yl, 3-(cyclohexen-1-yl)propyl, octadec-9-en-2-yl, and the like.

"Lower alkenyl" groups include those alkenyl groups of 2 to 7 carbon atoms. Examples of lower alkyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

The term "alkynyl" includes "lower alkynyl" and extends to cover carbon fragments having up to 20 carbon atoms. The acetylene group may be included within a ring structure of 10 members or more. Examples of alkynyl include dodec-2-yn-1-yl, 1-cyclohexylbut-1-yn-4-yl, cyclohexadecyn-3-yl, and the like.

"Lower alkynyl" groups include those alkynyl groups of 2 to 7 carbon atoms. Examples of lower alkynyl groups include ethynyl, propargyl, 3-methyl-1-pentynyl, 2-heptynyl, and the like.

The term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

The term "lower alkylsulfonyl" includes those alkyl sulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration the 2-butylsulfonyl group signifies $-S(O)_2CH(CH_3)CH_2CH_3$.

The term "lower alkylcarbonyl" includes those alkylcarbonyl groups of from 1 to 8 carbon atoms of a straight, branched or cyclic configuration. Examples of lower alkylcarboxyl groups are formyl, 2-methylbutanoyl, cyclohexylacetyl, etc. By way of illustration, the 2-methylbutanoyl group signifies $-C(O)CH(CH_3)CH_2CH_3$.

The terms $Ph(R^{10})_2$ and $Th(R^{10})_2$ indicate a phenyl or thienyl group substituted with two $R^{10}$ substituents.

Halogen means F, Cl, Br, and I.

It is intended that the definitions of any substituent (e.g., $R^1$, $R^2$, $Ph(R^{10})_2$ etc.) in a particular molecule be independent of its definitions elsewhere in the molecule. Thus, $-NR^{15}R^{15}$ represents $-NHH$, $-NHCH_3$, $-NHC_6H_5$, etc.

The heterocycles formed when two $R^{15}$ groups join through N are pyrrolidine, piperidine, morpholine, thiamorpholine, piperazine, and N-methylpiperazine.

The prodrug esters of Q (i.e., when $Q=CO_2R^{17}$) are intended to include the esters such as are described by Saari et al., *J. Med. Chem.*, 21, No. 8, 746–753 (1978), Sakamoto et al., *Chem. Pharm. Bull.*, 32, No. 6, 2241–2248 (1984) and Bundgaard et al., *J. Med. Chem.*, 30, No. 3, 451–454 (1987).

Within the definition of $R^{19}$, some representative monocyclic or bicyclic heterocyclic radicals are:
2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

The term standard amino acid is employed to include the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F. H. C. Crick, Symposium of the Society of Experimental Biology, 1958 (12), p. 140).

It is understood that $R^1$ and $R^2$ may be located at any unoccupied positions of the quinoline ring. The group $R^7$ replaces one of the $R^6$ groups attached to the carbons which make up ring A.

OPTICAL ISOMERS AND DIASTEREOMERS

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

UTILITIES

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |

| -continued | |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula 1 | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

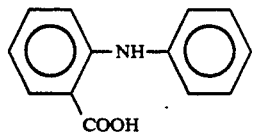

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

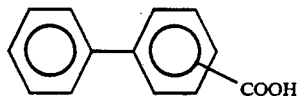

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

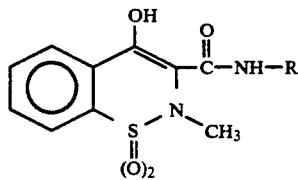

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP 56,172 (Jul. 21, 1982) and 61,800 (Jun. 10, 1982); and in U.K. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an H₁ or H₂-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K+/H+ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in U.K. Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the present invention can be prepared according to the following Schemes. Temperatures are in degrees Celsius.

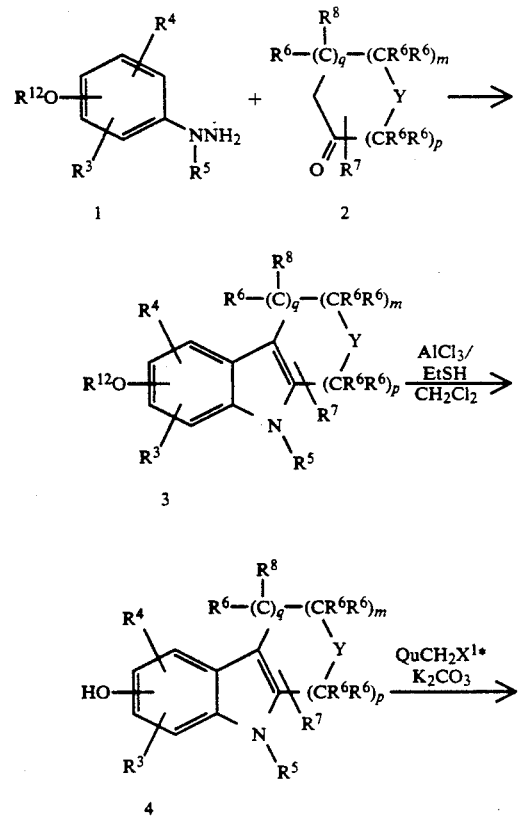

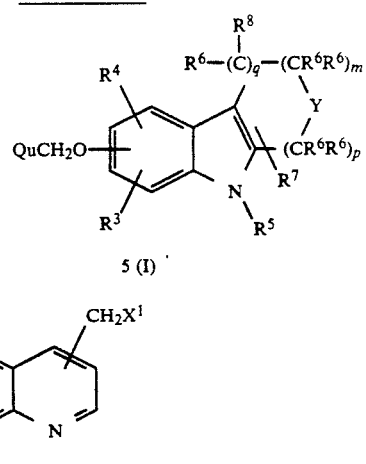

SCHEME 1

The starting oxygenated phenylhydrazines 1 are either commercially available or are described in the chemical literature. Thus EP 166,591 describes the preparation of 1 when $R^5$ is a substituted benzyl group. B. Robinson lists a number of phenylhydrazine derivatives of structure 1 in his book *The Fischer Indole Synthesis*, pp. 557–591, John Wiley & Sons, Toronto (1982).

Many ketones 2 are described in the chemical literature and many can be readily prepared by standard modifications of known procedures.

The halomethyl quinolines $QuCH_2X^1$ ($X^1$ is Cl, Br or I) are available from literature methods described in Quinolines, Parts I and II, G. Jones, Ed., John Wiley & Sons, Toronto (1977 and 1982). The preparation of $QuCH_2X^1$ by halogenation of the corresponding methyl quinolines is also described in the Jones volumes.

The phenylhydrazine 1 is made to undergo a Fischer indole reaction with ketone 2 in a suitable solvent such as acetic acid or formic acid. Alternatively, the hydrochloride salt of 1 will undergo the Fischer reaction with 2 in neutral solvents such as dimethylformamide, (DMF), ethanol, t-butanol, dioxane, etc., or in acetic acid. For further indications on the Fischer indole synthesis, see the above-mentioned book by B. Robinson or *Heterocyclic Compounds*, Volume 25, Parts I, II, III, W. J. Houlihan, Ed., Interscience, J. Wiley & Sons, New York (1979). If $R^{12}$ of 1 hydrogen, this reaction furnishes compound 4 directly. Compound 4 is prepared from 3 by dealkylation (or debenzylation when $R^{12}$ is a benzyl group) using an aluminum, gallium or boron halide in conjunction with an alkyl mercaptan in a neutral solvent such as benzene, $CH_2Cl_2$, $CH_2ClCH_2Cl$, etc. Phenol 4 is then coupled to the halomethylquinoline, $QuCH_2X^1$ by stirring the two together in a suitable solvent such as DMF, acetone, or N-methyl pyrrolidone (NMP), etc., in the presence of a base such as $K_2CO_3$, $KHCO_3$, $Na_2CO_3$ or $Cs_2CO_3$, etc. Product 5 is an example of a compound of the present invention. Compound 5 ($R^5$=H) can be reacted with various electrophiles, using potassium hexamethyldisilazide as base, and $R^5$—$X^1$ as electrophiles ($R^5$ not =H) to yield the N-substituted compounds 5 ($R^5$ not =H). If desired, Q in $R^7$ of 5 can be hydrolyzed to the corresponding carboxylic acid by standard procedures known in the art.

SCHEME 2

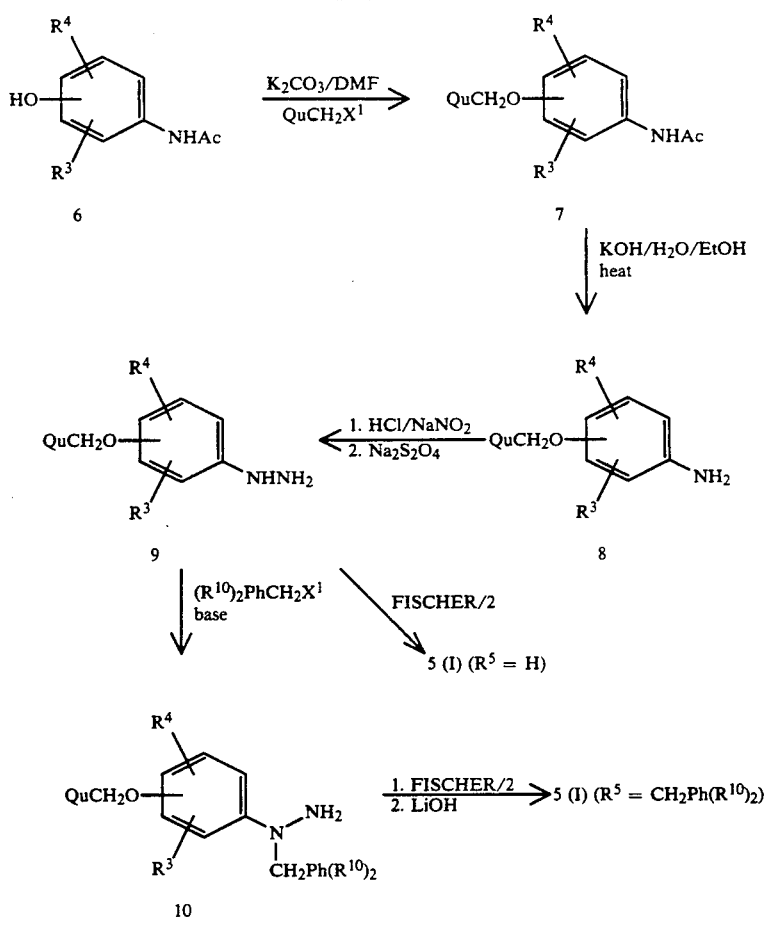

SCHEME 2

A suitable N-acetylated aminophenol 6 is reacted with $QuCH_2X^1$ using an alkali hydride or carbonate, such as potassium carbonate as a base in a polar solvent like DMF or NMP. The quinolinylmethoxy acetanilide 7 is then de-acetylated using standard basic conditions, preferably using alcoholic potassium hydroxide under reflux to produce the quinolinylmethoxy aniline derivative 8. Conversion of the quinolinylmethoxy aniline derivative to the hydrazine analogue 9 is effected through reduction of the intermediate diazonium salt using sodium hydrosulfite in an aqueous medium.

The hydrazine 9 is then N-benzylated using a benzyl halide in an organic solvent such as methylene chloride containing an amine base such as diisopropylethylamine and preferably tetra-n-butylammonium bromide as catlyst.

The hydrazine 10 is then processed using a Fischer indolization with ketone 2 according to Scheme 1 to produce compound 5 of the present invention.

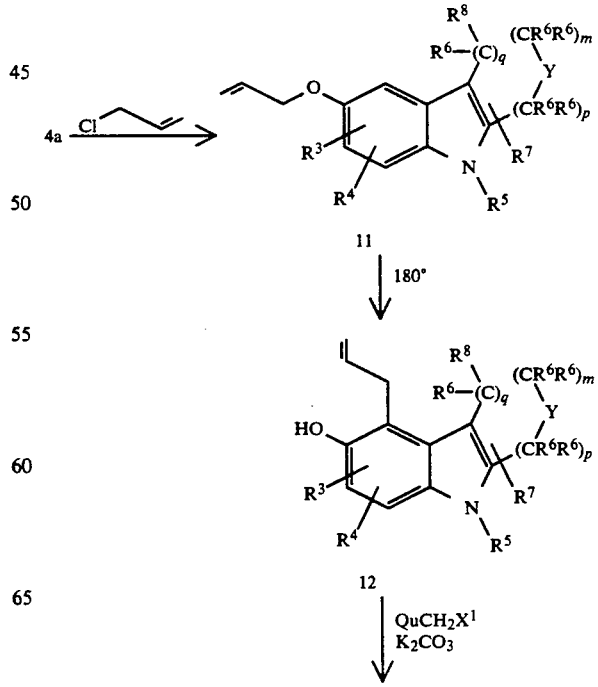

-continued
SCHEME 3

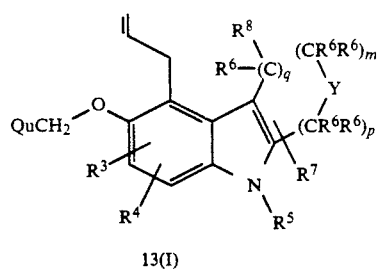

13(I)

SCHEME 3

Scheme 3 illustrates the introduction of an allyl group into compounds of the present invention. The method indicated through the intermediates 11 and 12 is known as the Claisen rearrangement, and is well described in the art: S. J. Rhoads and N. R. Raulins, *The Claisen and Cope Rearrangements*, in *Organic Reactions*, Vol. 22, pp. 1-252 (1975). The allyl group can in turn be converted into many other functionalities by standard procedures of organic chemistry (e.g. hydroboration, reduction, epoxidation, oxidative cleavage, etc.).

SCHEME 4

A synthesis of 2-oxa-1,2,3,4-tetrahydrocarbazoles is indicated Scheme 4, wherein the 3-ethanol derivative of an indole 14 is condensed with the ketoester 15 under acid catalysis. This methodology is described by D. Mobilio, et al., *J. Med. Chem.*, 31, 2211-2217 (1988) and references cited therein. The product 16 can be hydrolyzed to the corresponding acid if desired.

SCHEME 4

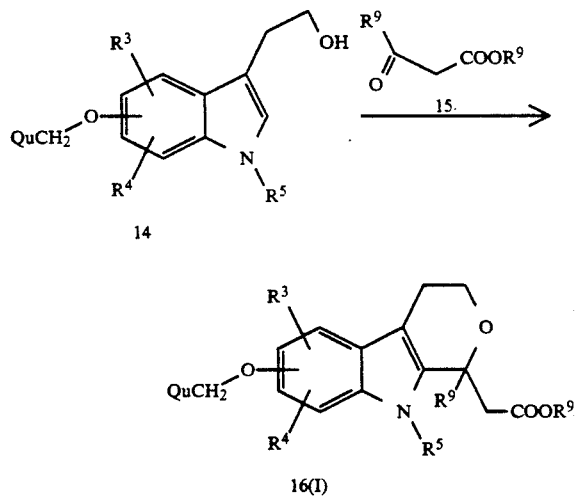

SCHEME 5

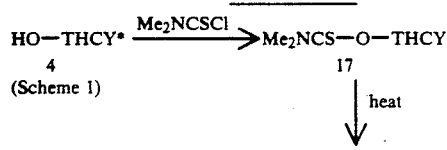

-continued
SCHEME 5

$$HS-THCY \xleftarrow{MeONa}{MeOH} Me_2NCO-S-THCY$$
19        18

$$\downarrow QuCH_2X^1 \text{ Base}$$

$$QuCH_2S-THCY \xrightarrow{H_2O_2}{HOAc} QuCH_2S(O)_2-THCY$$
20 (I)        21 (I)

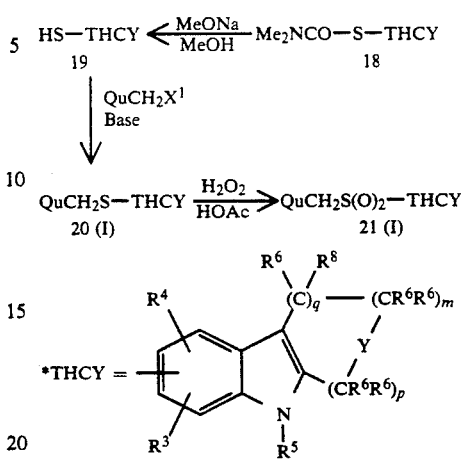

*THCY =

SCHEME 5

In Scheme 5 the routes used to prepare compounds of Formula I where $X^2-X^3=-CH_2S-$ are described. As the first step, the indole 4 (from Scheme 1) is dissolved in an organic solvent (e.g., DMF) and is treated with an inorganic base such as NaH followed by the addition of dimethylthiocarbamoyl chloride to provide the intermediate 17. Heating intermediate 17 neat causes the compound to rearrange to give the thiophenol derivative 18. This compound when refluxed in a solution of, for example, sodium methoxide in methanol followed by reduction of the disulfide bond if necessary (triphenylphosphine, 6N HCl in an organic solvent such as dioxane) gives the thiophenol 19. The thiol group of intermediate 19 may be alkylated by stirring a solution of thiophenol 19, a base such as $K_2CO_3$ or triethylamine, and an appropriate alkylating agent, $QuCH_2X^1$ in a solvent such as THF. This procedure affords the product 20, which is an example of compound I of the present invention.

Oxidation of 20 with two equivalents of mild oxidizing agent such as hydrogen peroxide in acetic acid or meta-chloroperbenzoic acid in methylene chloride will yield the corresponding sulfone 21.

SCHEME 6

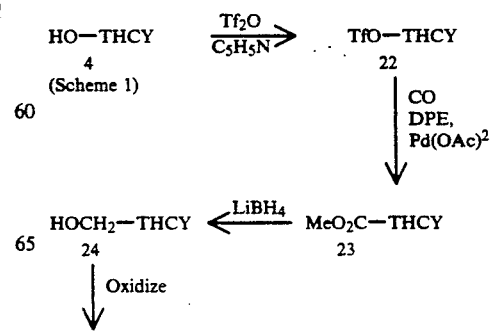

-continued
SCHEME 6

OHC—THCY $\xrightarrow[\text{BuLi}]{\text{QuCH}_2\text{P(Ph)}_3\text{X}^1}$ QuCH=CH—THCY
25                                                26 (I)

$\downarrow$ H$_2$ Pd/C

Qu—CH$_2$CH$_2$—THCY
27 (I)

SCHEME 6

Compounds of Formula I where $X^2X^3$=—CH=CH— or —(CH$_2$)$_2$— are prepared according to Scheme 6. The phenol 4 (from Scheme 1) may be converted to the triflate 22 by stirring with trifluoromethanesulfonic anhydride (Tf$_2$O), and an organic base (e.g., pyridine) in a solvent such as dichloromethane. A solution of the triflate 22 in DMSO/methanol as solvent with an organic base such as triethylamine, a phosphine such as diphenylphosphinoethane (DPE), a palladium II salt (e.g., palladium(II) acetate), and an atmosphere of carbon monoxide gives the ester 23.

Reaction of ester 23 with a reducing agent, e.g. lithium borohydride, in an organic solvent such as THF yields alcohol 24.

Alcohol 24 may be oxidized using, for example, manganese dioxide in an organic solvent such as dichloromethane to produce aldehyde 25. A Witting reaction between aldehyde 21 and an ylid derived from deprotonation of a phosphonium salt, QuCH$_2$P(C$_6$H$_5$)$_3$X$^1$, using an inorganic base (e.g., n-BuLi) in an organic solvent such as THF affords the unsaturated product 26. Compound 26 may be hydrogenated in an alcoholic solvent (e.g., methanol) using a catalyst such as 10% palladium on carbon and a hydrogen atmosphere to yield the saturated product 27.

Q in R$^7$ in compounds 20, 21, 26, or 27 can be hydrolyzed to the corresponding carboxylic acid by standard procedures known in the art.

REPRESENTATIVE COMPOUNDS

Table I illustrates compounds representative of the present invention having the generic formula I$_b$.

ASSAYS FOR DETERMINING BIOLOGICAL ACTIVITY

Two assays can be used to measure cytoprotective ability. These assays are; (A) an ethanol-induced lesion assay and (B) an indomethacin-induced ulcer assay and are described in EP 140,684.

Compounds of Formula I can be tested using the following assays to determine their mammalian leukotriene biosynthesis inhibiting activity.

RAT PERITONEAL POLYMORPHONUCLEAR (PMN) LEUKOCYTE ASSAY

Rats under ether anesthesia are injected (i.p.) with 8 mL of a suspension of sodium caseinate (6 grams in ca. 50 mL water). After 15–24 hr. the rats are sacrificed (CO$_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 μL aliquot of PMN suspension and test compound are preincubated for 2 minutes at 37°, followed by the addition of 10 μM A-23187. The suspension is stirred for an additional 4 minutes then bioassayed for LTB$_4$ content by adding an aliquot to a second 500 μL position of the PMN at 37° C. The LTB$_4$ produced in the first incubation causes aggregation of the second PMN, which is measured as a change in light transmission. The size of the assay aliquot is chosen to give a submaximal transmission change (usually −70%) for the untreated control. The percentage inhibition of LTB$_4$ formation is calculated from the ratio of transmissin change in the sample to the ratio of transmission change in the compound-free control.

HUMAN POLYMORPHONUCLEAR (PMN) LEUKOCYTE LTB$_4$ ASSAY

A. Preparation of Human PMN. Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at 5×10$^5$ cells/mL in HEPES (15 mM)-buffered Hanks

TABLE 1

| Ex | R$^5$ | R$^7$ | (CR$^6$R$^6$)$_p$ | Y | (CR$^6$R$^6$)$_m$ | (R$^6$CR$^8$)$_q$ |
|---|---|---|---|---|---|---|
| 1 | p-ClBz | 1-CH$_2$CO$_2$H | (CH$_2$)$_2$ | O | — | HCH |
| 2 | p-ClBz | 1-CH$_2$CO$_2$H | (CH$_2$)$_2$ | O | — | HC-p-ClPh |
| 3 | p-MeSBz | 1-CH$_2$CO$_2$H | (CH$_2$)$_2$ | S | — | HCH |
| 4 | p-MeS(O)$_2$Bz | 1-CH$_2$CO$_2$H | (CH$_2$)$_2$ | S(O)$_2$ | — | HCH |
| 5 | p-ClBz | 1-CH$_2$CO$_2$H | (CH$_2$)$_3$ | S | — | — |
| 6 | p-ClBz | 1-CH$_2$CO$_2$H | (CH$_2$)$_3$ | S(O)$_2$ | — | — |
| 7 | p-ClBz | 1-CH$_2$CO$_2$H | CHEt | O | CH$_2$ | HCH |
| 8 | p-ClBz | 1-CH$_2$CO$_2$H | CHEt | O | CH$_2$ | HCBz | balanced salt solution containing $Ca^{2+}$ (1.4 mM) and $Mg^{2+}$ (0.7 mM), pH 7.4. Viability was assessed by Trypan blue exclusion and was typically greater than 98%.
(1) Boyum, A. Scand. J. Clin. Lab. Invest. 21, (Supp 97), 77, (1968).

B. Generation and Radioimmunoassay of $LTB_4$. PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore A23187 (final concentration 10 $\mu$M) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 $\mu$L) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter $[^3H]$-$LTB_4$ (10 nCi in 100 $\mu$L RIA buffer) and $LTB_4$-antiserum (100 $\mu$L of a 1:3000 dilution in RIA buffer) were added and the tubes vortexed. Reactants were allowed to equilibrate by incubation overnight at 4° C. To separate antibody-bound from free $LTB_4$, aliquots (50 $\mu$L) of activated charcoal (3% activated charcoal in RIA buffer containing 0.25% Dextran T-70) were added, the tubes vortexed, and allowed to stand at room temperature for 10 minutes prior to centrifugation ($1500 \times g$; 10 min; 4° C). The supernatants containing antibody-bound $LTB_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of $LTB_4$ produced in test and control (approx. 20 ng/$10^6$ cells) samples were calculated. Inhibitory dose-response curves were constructed using a four-parameter algorithm and from these the $IC_{50}$ values were determined.
(2) Rokach, J.; Hayes, E. C.; Girard, Y.; Lombardo, D. L.; Maycock, A. L.; Rosenthal, A. S.; Young, R. N.; Zamboni, R.; Zweerink, H. J. Prostaglandins Leukotrienes and Medicine 13, 21, (1984).

ASTHMATIC RAT ASSAY

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 $\mu$gm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

What is claimed is:

1. A compound of the formula:

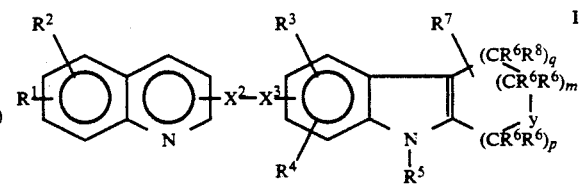

wherein:

each of $R^1$, $R^2$, $R^3$, $R^4$ and $R^{10}$ is independently hydrogen, halogen, lower alkyl, lower alkenyl, lower alkynyl, $-CF_3$, $-CN$, $-NO_2$, $-N_3$, $-C(OH)R^6R^6$, $-C(O)OR^{12}$, $-SR^{13}$, $-S(O)R^{13}$, $-S(O)_2R^{13}$, $-S(O)_2NR^{15}R^{15}$, $-C(O)NR^{15}R^{15}$, $-OR^{15}$, $-NR^{15}R^{15}$, $-C(O)R^{16}$ or $-(CH_2)_rR^{21}$;

$R^5$ is hydrogen or $X-R^9$, $R^6$ is independently hydrogen or lower alkyl, or two $R^6$ groups on the same carbon atom are joined to form a cycloalkyl ring of 3 to 6 carbon atoms;

$R^7$ is $-(CR^6R^6)_sQ$;

$R^8$ is hydrogen, $R^9$, $-CR^{23}=CR^{24}R^{25}$, $-C(Cl)=CCl_2$ or $R^6$ plus $R^8$ on the same carbon atom may be a double bonded oxygen ($=O$);

$R^9$ is alkyl, alkenyl, $-(CH_2)_tPh(R^{10})_2$ or $-(CH_2)_tTh(R^{10})_2$;

$R^{11}$ is the structure of a standard amino acid except for the amino group $\alpha$ to the carboxy group, or $R^{11}$ and $R^{18}$ attached to the same nitrogen can cyclize to form a proline residue;

$R^{12}$ is hydrogen, lower alkyl or $-CH_2R^{21}$;

$R^{13}$ is $-CF_3$ or $R^{14}$;

$R^{14}$ is lower alkyl or $-(CH_2)_uR^{21}$;

$R^{15}$ is hydrogen, —C(O)$R^{16}$, $R^{14}$, or two $R^{15}$ groups on the same nitrogen may be joined to form a heterocyclic ring of 4 to 6 atoms containing up to 2 heteroatoms chosen from O, S or N;

$R^{16}$ is hydrogen, lower alkenyl, lower alkynyl, or $R^{13}$;

$R^{17}$ is —(CH$_2$)$_r$—C($R^{18}R^{18}$)—(CH$_2$)$_r$—$R^{19}$ or —CH$_2$-C(O)NR$^{15}$R$^{15}$;

$R^{18}$ is hydrogen or lower alkyl;

$R^{19}$ is
 a) a monocyclic or bicyclic heterocyclic radical containing from 3 to 9 nuclear carbon atoms and 1 or 2 nuclear hetero-atoms selected from N, S or O and with each ring in the heterocyclic radical being formed of 5 or 6 atoms, or
 b) the radical W-$R^{20}$;

$R^{20}$ contains up to 21 carbon atoms and is (1) a hydrocarbon radical or (2) an acyl radical of an organic acyclic or monocyclic carboxylic acid containing not more than 1 heteroatom in the ring;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, —CF$_3$, —CN, —NO$_2$ or —N$_3$;

$R^{23}$ is $R^{18}$ or $R^{23}$ and $R^{24}$ may form a bond;

$R^{24}$ is $R^6$ or $R^{23}$ and $R^{24}$ may form a bond;

$R^{25}$ is $R^6$;

m is 0 to 3;

p is 1 to 3 q is 0 or 1;

m+p+q is 2 to 4;

m+q is 0 to 3;

r is 0 to 2;

s is 0 to 4;

t is 0 to 3;

u is 0 to 3;

v is 0 to 3;

W is O, S, or NR$^{15}$;

X is C(O), CR$^6$R$^6$, S(O)$_2$, or a bond;

$X^2$—$X^3$ is CH$_2$O, CH$_2$S, CH$_2$S(O)$_2$, CH$_2$CH$_2$, or CH=CH;

Y is O, NR$^{15}$, S, S(O), or S(O)$_2$;

Q is —C(O)NR$^{11}$R$^{18}$ —C(O)OR$^{12}$, —C(O)NH-S(O)$_2$R$^{13}$, —NHS(O)$_2$R$^{13}$, —S(O)$_2$NHR$^{15}$, —C(O)NR$^{15}$R$^{15}$, —C(O)OR$^{17}$, —CH$_2$OH, or 1H- or 2H-tetrazol-5-yl;

or the pharmaceutically acceptable salts thereof.

2. A compound of claim 1 wherein:
each of $R^1$, $R^2$, $R^3$ and $R^4$ is hydrogen;
$R^5$ is X-$R^9$;
$R^8$ is $R^9$;
$R^{10}$ is hydrogen or halogen;
the CH$_2$O is attached to the 2-position of the quinoline ring;
X is a bond; and
$X^2$—$X^3$ is CH$_2$O;
Q is —C(O)OR$^{12}$.

3. A compound of claim 1 of formula Ib wherein the substituents are as follows:

| | $R^5$ | $R^7$ | (CR$^6$R$^6$)$_p$ | Y | (CR$^6$R$^6$)$_m$ | (R$^6$CR$^8$)$_q$ |
|---|---|---|---|---|---|---|
| 1 | p-ClBz | 1-CH$_2$CO$_2$H | (CH$_2$)$_2$ | O | — | HCH |
| 2 | p-ClBz | 1-CH$_2$CO$_2$H | (CH$_2$)$_2$ | O | — | HC-p-ClPh |
| 3 | p-MeSBz | 1-CH$_2$CO$_2$H | (CH$_2$)$_2$ | S | — | HCH |
| 4 | p-MeS(O)$_2$Bz | 1-CH$_2$CO$_2$H | (CH$_2$)$_2$ | S(O)$_2$ | — | HCH |
| 5 | p-ClBz | 1-CH$_2$CO$_2$H | (CH$_2$)$_3$ | S | — | — |
| 6 | p-ClBz | 1-CH$_2$CO$_2$H | (CH$_2$)$_3$ | S(O)$_2$ | — | — |
| 7 | p-ClBz | 1-CH$_2$CO$_2$H | CHEt | O | CH$_2$ | HCH |
| 8 | p-ClBz | 1-CH$_2$CO$_2$H | CHEt | O | CH$_2$ | HCBz |

4. A pharmaceutical composition comprising a therapeutically effective amount of a compound of claim 1 and a pharmaceutically acceptable carrier.

5. A method of preventing the synthesis, the action, or the release of SRS-A or leukotrienes in a mammal which comprises administering to said mammal an effective amount of a compound of claim 1.

6. The method of claim 5 wherein the mammal is man.

7. A method of treating asthma in a mammal comprising administering to a mammal in need of such treatment a therapeutically effective amount of a compound of claim 1.

* * * * *